(12) United States Patent
Quinlan et al.

(10) Patent No.: US 10,610,375 B2
(45) Date of Patent: Apr. 7, 2020

(54) SPINAL FUSION DEVICE AND METHOD OF USING SAME

(71) Applicants: Raymond J. Quinlan, Stonington, CT (US); Michael J. Halperin, Groton, CT (US)

(72) Inventors: Raymond J. Quinlan, Stonington, CT (US); Michael J. Halperin, Groton, CT (US)

( * ) Notice: Subject to any disclaimer, the term of this patent is extended or adjusted under 35 U.S.C. 154(b) by 0 days.

(21) Appl. No.: 14/829,911

(22) Filed: Aug. 19, 2015

(65) Prior Publication Data

US 2017/0049579 A1    Feb. 23, 2017

(51) Int. Cl.
| | |
|---|---|
| A61F 2/44 | (2006.01) |
| A61F 2/46 | (2006.01) |
| A61B 17/16 | (2006.01) |
| A61F 2/28 | (2006.01) |
| A61F 2/30 | (2006.01) |
| A61B 17/86 | (2006.01) |
| A61B 17/80 | (2006.01) |

(52) U.S. Cl.
CPC .......... *A61F 2/447* (2013.01); *A61B 17/1604* (2013.01); *A61B 17/8042* (2013.01); *A61B 17/86* (2013.01); *A61F 2002/2835* (2013.01); *A61F 2002/3052* (2013.01); *A61F 2002/30202* (2013.01); *A61F 2002/30383* (2013.01); *A61F 2002/30578* (2013.01); *A61F 2002/30772* (2013.01); *A61F 2002/30787* (2013.01); *A61F 2002/30904* (2013.01); *A61F 2002/4475* (2013.01); *A61F 2002/4602* (2013.01)

(58) Field of Classification Search
CPC .......... A61F 2/44; A61F 2/4455; A61F 2/446; A61F 2/4465; A61F 2/447; A61F 2/4405; A61F 2002/4475; A61F 2002/4602; A61B 17/8095
See application file for complete search history.

(56) References Cited

U.S. PATENT DOCUMENTS 5,674,296 A * 10/1997 Bryan .................. A61B 17/686
606/247
5,702,454 A   12/1997 Baumgartner
5,888,223 A *  3/1999 Bray, Jr. ................. A61F 2/442
606/247

(Continued)

FOREIGN PATENT DOCUMENTS

WO    WO 2012056119 A1 *  5/2012 ............. A61F 2/447

OTHER PUBLICATIONS

Translation of WO2012056119A1.*

(Continued)

*Primary Examiner* — Lynnsy M Summitt
(74) *Attorney, Agent, or Firm* — Carmody Torrance Sandak & Hennessey LLP

(57) ABSTRACT

A spinal fusion device having a spacer and a fastener and an associated method of use are disclosed. The spinal fusion device preferably has features to prevent excessive insertion of the spacer between two adjacent vertebrae, to ensure proper fenestration, to ensure tight engagement between the spacer and the fastener and between the spinal fusion device and two adjacent vertebrae, to hinder back-out of screws used by the fastener, and to promote compaction and displacement of bone graft material to enhance the fusion process.

18 Claims, 15 Drawing Sheets

(56) References Cited

U.S. PATENT DOCUMENTS

| | | | |
|---|---|---|---|
| 6,059,829 A * | 5/2000 | Schlapfer | A61F 2/4455 606/247 |
| 6,066,175 A * | 5/2000 | Henderson | A61F 2/44 623/17.11 |
| 6,245,108 B1 * | 6/2001 | Biscup | A61F 2/4455 606/246 |
| 6,682,561 B2 * | 1/2004 | Songer | A61B 17/70 623/16.11 |
| 7,169,183 B2 * | 1/2007 | Liu | A61F 2/447 623/17.16 |
| 7,232,463 B2 * | 6/2007 | Falahee | A61B 17/1757 623/17.11 |
| 7,276,082 B2 | 10/2007 | Zdeblick et al. | |
| 7,641,690 B2 * | 1/2010 | Abdou | A61F 2/442 623/17.11 |
| 7,674,297 B2 | 3/2010 | Falahee | |
| 7,678,148 B2 | 3/2010 | Peterman | |
| 7,862,615 B2 | 1/2011 | Carli et al. | |
| 8,273,127 B2 | 9/2012 | Jones et al. | |
| 8,377,132 B2 * | 2/2013 | Wing | A61F 2/4465 623/17.11 |
| 8,430,882 B2 * | 4/2013 | Lowry | A61B 17/1671 606/86 R |
| 8,491,658 B1 * | 7/2013 | Etminan | A61F 2/442 623/17.16 |
| 8,641,765 B2 | 2/2014 | Muhanna | |
| 8,821,553 B2 * | 9/2014 | Kirschman | A61B 17/7059 606/294 |
| 8,932,358 B1 | 1/2015 | Nehls | |
| 8,945,227 B2 * | 2/2015 | Kirschman | A61F 2/44 606/99 |
| 9,005,292 B2 | 4/2015 | Melamed | |
| 9,078,706 B2 * | 7/2015 | Kirschman | A61B 17/7059 |
| 9,114,023 B2 * | 8/2015 | Kana | A61F 2/4465 |
| 9,161,841 B2 * | 10/2015 | Kana | A61F 2/4465 |
| 9,387,087 B2 * | 7/2016 | Tyber | A61F 2/4455 |
| 9,402,738 B2 * | 8/2016 | Niemiec | A61F 2/4455 |
| 2002/0035400 A1 | 3/2002 | Bryan et al. | |
| 2002/0161444 A1 * | 10/2002 | Choi | A61F 2/446 623/17.11 |
| 2005/0228500 A1 | 10/2005 | Kim et al. | |
| 2006/0074488 A1 * | 4/2006 | Abdou | A61F 2/44 623/17.11 |
| 2009/0105825 A1 | 4/2009 | Foreman et al. | |
| 2009/0210062 A1 | 8/2009 | Thalgott et al. | |
| 2010/0042216 A1 * | 2/2010 | Kilpela | A61F 2/446 623/17.11 |
| 2011/0251689 A1 | 10/2011 | Seifert et al. | |
| 2012/0197399 A1 * | 8/2012 | Kirschman | A61B 17/7059 623/17.11 |
| 2012/0277873 A1 * | 11/2012 | Kana | A61F 2/447 623/17.16 |
| 2013/0297029 A1 * | 11/2013 | Kana | A61F 2/447 623/17.16 |
| 2014/0012384 A1 | 1/2014 | Kana et al. | |
| 2014/0228959 A1 * | 8/2014 | Niemiec | A61F 2/4455 623/17.16 |
| 2014/0277456 A1 * | 9/2014 | Kirschman | A61F 2/4455 623/17.11 |
| 2015/0032220 A1 * | 1/2015 | Tyber | A61B 90/94 623/23.5 |
| 2015/0289989 A1 * | 10/2015 | Abdou | A61F 2/442 623/17.16 |

OTHER PUBLICATIONS

"Prestige® LP Cervical Disc System Surgical Technique," Medtronic Sofamor Danek USA, Inc. (2014), 21 pages. Admitted prior art.

"ROIC® CervicalCage," LDR PDF document, 4 pages. Admitted prior art.

"Coalition ACDF System," www.globusmedical.com, 2 pages. Admitted prior art.

"Product Line—The Next Generation of Interbody Devices: Active Participants in the Fusion Process," Titan Spine, PDF document, 2 pages. Admitted prior art.

"ACIS™ Anterior Cervical Interbody Spacer," 2 pages. Admitted prior art.

"Dynamic Cervical Implant DCI," Paradigm Spine, PDF document, 20 pages. Admitted prior art.

"Interlaminar Implant Coflex," Paradigm Spine, PDF document, 17 pages. Admitted prior art.

* cited by examiner

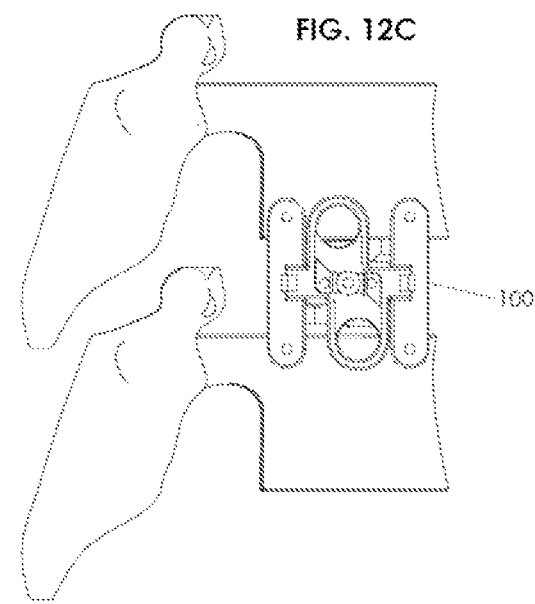

SPINAL FUSION DEVICE AND METHOD OF USING SAME

BACKGROUND OF THE INVENTION

The present invention relates generally to the field of spinal fusion and specifically spinal fusion devices and associated methods.

The human spine comprises a series of alternating vertebrae and discs. Herniated discs, bone spurs, degenerated discs, or other conditions that result in nerve root or spinal cord compression can cause severe pain and dysfunctional spinal conditions. Such conditions include, but are not limited to, axial back or neck pain, cervical or lumbar radiculitis/radiculopathy, cervical or lumbar deformity, cervical or lumbar spondylosis, stenosis, discogenic pain, myelopathy, and headaches. Spinal fusion is a common surgical technique to alleviate this pain and requires the permanent joining of two adjacent vertebrae via a bone graft (supplemental bone tissue). In an interbody spinal fusion procedure, a surgeon will first remove a troublesome disc from between two vertebrae and replace the disc with a bone graft. It is the goal of this procedure for the bone graft to work in conjunction with the natural tissue in the vertebrae to form new bone material, fusing the two vertebrae together. If the fusion does not take, i.e., bone does not completely grow across the interspace between vertebrae, this could result in pain for the patient, hardware failure, and/or a need for further surgery.

Frequently, spinal instrumentation will be included in the fusion procedure. Various implants have been developed to improve the quality of the grafting process and ensure a successful fusion. It is important that such implants (i) provide a vehicle to hold the bone graft material in place between the two vertebrae, (ii) immobilize the vertebra-graft-vertebra segment so that fusion may occur, (iii) maintain proper disc height for the removed disc, and (iv) maintain or restore proper alignment of the spine.

One implant device uses a combination of a separate plate and spacer. The spacer is prepackaged with bone or bone substitute and is inserted into the space between the vertebrae, and a plate that accepts four screws (two into each vertebrae) is fastened over the spacer. However, the plates used in these implants (i) can impinge upon adjacent discs or vertebrae, (ii) can pose alignment difficulties, and (iii) require more dissection and retraction during the surgery.

Another implant utilizes a plate preassembled with a spacer. These implants have the advantages of less dissection, ease of insertion, and a speedier surgical procedure. However, they have significant drawbacks in that they generally only have one screw per vertebrae, and the bone graft material must be pre-inserted into the spacer, which would not allow for in situ adjustments. Additionally, with low profile devices where the plate does not extend over the anterior surface of the vertebral bodies, the screws must be inserted at difficult angles in these apparatuses.

SUMMARY AND OBJECTIVES OF THE INVENTION

The present invention solves for a need in the art for a spinal fusion implant device that improves upon prior art implants. In a preferred embodiment, the invention is directed to a spinal fusion device kit comprising: a back-fillable spacer, having a posterior portion and an anterior portion, the back-fillable spacer configured to fit between two adjacent vertebrae; a fastener, having a posterior side and an anterior side, the fastener configured to engage the anterior portion of the spacer and configured to be fastened to two adjacent vertebrae; and a plurality of spacer protrusions coupled to the anterior portion of the spacer and extending in at least one of a superior and an inferior direction, wherein the plurality of spacer protrusions are configured to engage an anterior portion of two adjacent vertebrae.

In another preferred embodiment, the invention is directed to a spinal fusion device kit comprising: a back-fillable spacer, having a posterior portion and an anterior portion, the back-fillable spacer configured to fit between two adjacent vertebrae; and a fastener, having a posterior side and an anterior side, the fastener configured to engage the anterior portion of the spacer and configured to be fastened to two adjacent vertebrae; wherein the fastener has at least one fastener protrusion, protruding from the posterior side of the fastener, and configured to displace fusion material within a cavity defined by the spacer.

In another preferred embodiment, the invention is directed to a method for fusing adjacent vertebrae. The method contemplated by the present invention comprises the steps of: (1) inserting a back-fillable spacer having a posterior portion and an anterior portion between two adjacent vertebrae comprising a superior vertebra having an inferior endplate and an inferior vertebra having a superior endplate; (2) inserting bone graft material between the two adjacent vertebrae and into a cavity defined by the spacer; (3) engaging a fastener having a posterior side and an anterior side with the anterior portion of the spacer; and (4) fastening the fastener to the two adjacent vertebrae, wherein the spacer has a plurality of spacer protrusions, protruding from the anterior portion of the spacer and extending in at least one of a superior and an inferior direction, and wherein the plurality of spacer protrusions are configured to engage an anterior portion of the two adjacent vertebrae.

As used in the present invention, the terms posterior, anterior, superior, inferior, and lateral are made with reference to the contemplated positioning of the device in the human body. Thus, anterior means the direction toward the front of the human body, for example the chest. Posterior means the direction toward the back of the human body, for example, the back. Superior means the direction toward the top of the human body, for example, the head. Inferior means the direction toward the bottom of the human body, for example, the feet. Lateral means the direction away from the center of the human body towards its sides, for example, to the left and right of midline. Medial means the direction towards the center of the human body from its sides.

Disclosed advantages and benefits may apply to only certain embodiments of the invention and should not be used to limit the invention, which is defined solely by the claims. In the preferred embodiments, some objectives of the invention include, but are not limited to, providing a spacer that is back-fillable, such that bone graft material can be placed into the spacer after the spacer is inserted into the space between the two vertebrae; ensuring, through the use of the spacer protrusions, that the spacer is not inserted too far in a posterior direction into the space between the two vertebrae; efficiently and effectively immobilizing the vertebra-graft-vertebra segment to facilitate the fusion process; maintaining proper alignment of the spine and preserving proper height of the vertebra-disc-vertebra unit; and minimizing the profile of the implant and the length of the required surgical procedure.

Other objectives of the invention will be apparent from the following detailed description of the preferred embodiments of the invention.

BRIEF DESCRIPTION OF THE DRAWINGS

The preferred embodiments of the invention are described with reference to the accompanying figures. These figures, incorporated herein and forming part of the specification, illustrate embodiments of the invention and, together with the description, further explain its principles enabling a person skilled in the art to make and use the invention, wherein:

FIGS. 12A, 12B and 12C illustrate a preferred embodiment of the present invention that would be utilized in a lateral interbody fusion procedure.

Although like numbers refer to like parts and features in the figures, not all parts and features are labeled in each figure.

DETAILED DESCRIPTION OF THE PREFERRED EMBODIMENTS OF THE INVENTION

The disclosure provided herein describes examples of the preferred embodiments of the invention. The designs, figures, and descriptions are non-limiting examples of the embodiments they disclose. For example, other embodiments of the disclosed device and/or method may or may not include all of the features described herein.

Figure 3:
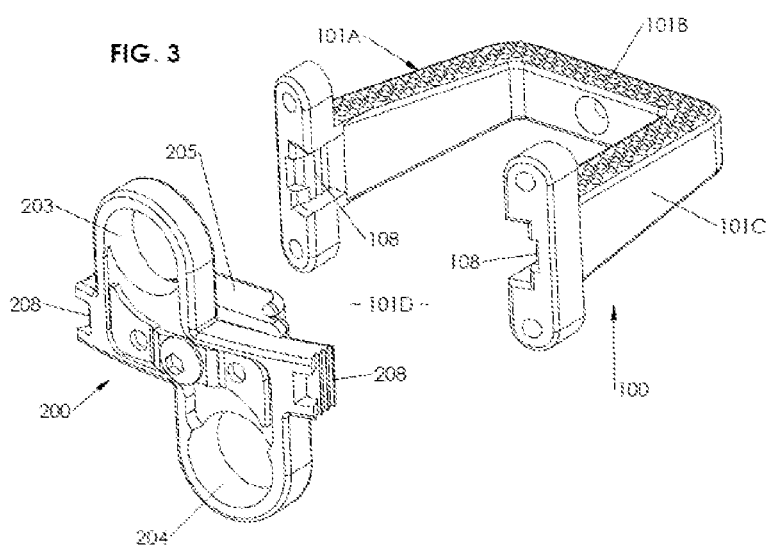
FIG. 3 is a perspective view of a preferred embodiment of the spinal fusion device contemplated within the present invention in an unassembled state.
Figure 4:
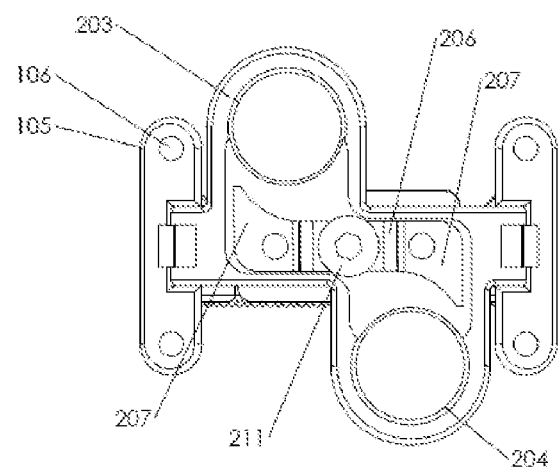
FIG. 4 is a front view of a preferred embodiment of the spinal fusion device contemplated within the present invention in an assembled state.
Figure 5:
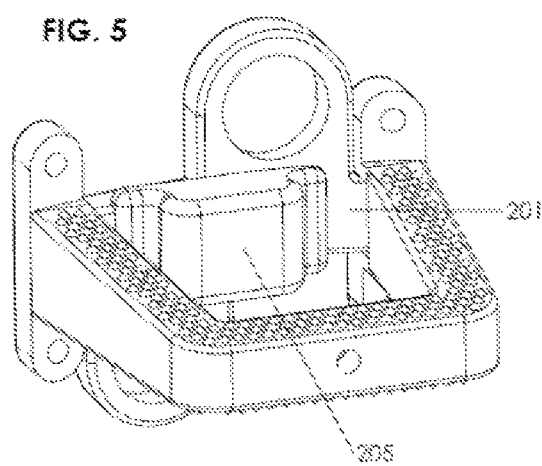
FIG. 5 is a rear perspective view of a preferred embodiment of the spinal fusion device contemplated within the present invention in an assembled state.

In a first preferred embodiment, the invention may comprise a back-fillable spacer, generally indicated at 100. This can be made out of peek, carbon fiber, titanium, other metallic or rigid materials, or a combination of the foregoing. If peek or carbon fiber or other radiolucent material is utilized, then markers made out of tantalum or another radio opaque metal or substance could be incorporated to assist with radiographic localization and positioning of the implants. The spacer has a posterior portion 101 and an anterior portion 102. The spacer can have many shapes, including circular, ovular, square, rectangular, freeform, or trapezoidal. However, the anterior portion 102 of the spacer 100 is generally, at least partially open. The spacer also preferably defines a cavity 109. Bone graft material, indicated generically by reference number 110 (FIG. 8) is inserted between the two adjacent vertebrae and into cavity 109 defined by the spacer preferably after the spacer is inserted between two vertebrae. A "cavity" may be any space bounded on any one or more sides by any one or more portions (e.g. sections 101A, 101B, 101C) of the spacer 100. Preferably, the spacer 100 is U shaped or if of another of the aforementioned shapes, missing its anterior side so as to provide an opening side 101D, for example as shown in FIG. 3. It is preferred that the spacer 100 have a thickness in the superior-inferior dimension approximately equivalent to the thickness of a disc between two vertebrae. This will allow the spacer to maintain the overall thickness of the vertebra-disc-vertebra unit. The spacer is preferably weight bearing so that it will resist subsidence by the vertebrae. The superior surface and/or the inferior surface of the spacer 100 is preferably textured 103. The texture 103 can improve the frictional engagement of the spacer 100 with the two vertebrae to prevent migration or movement of the implant. Additionally, the texture 103 can facilitate the fusion process by abrading the endplates of the two vertebrae. "Endplates" refer to the two surfaces of the two vertebrae between which the implant is fitted, which can be coated with titanium (or other material, such as hydroxyapatite (HA)) spray.

The spacer 100 may also preferably comprise a gouge aligner 104, preferably positioned in the posterior portion of the spacer 100. The gouge aligner 104 can be a hole, a tab, a peg, a spike, or any feature that will facilitate alignment of a gouge during the surgery. A gouge is a medical instrument used during the spinal fusion surgery. Generally, after insertion of the spacer 100, but before insertion of the bone graft, a gouge is inserted into the spacer and manipulated to promote endplate fenestration. In essence, the endplates of the two vertebrae are abraded with the gouge so that the bone graft material can more efficiently and effectively blend with the cancellous bone of the adjacent vertebrae in order to bring in better blood supply to the graft to promote and enhance the likelihood of successful solid fusion. The gouge aligner 104 may aid the surgeon in orienting the gouge during this process. Additionally, the gouge aligner 104 may allow the gouge to fenestrate in the middle portion of the endplates, i.e., in the portions of the endplates adjoining the cavity formed by the spacer 100. This can be accomplished while preserving the important peripheral portions of the vertebral endplates so as to reduce the risk of implant subsidence into the vertebral bodies.

Figure 11A:
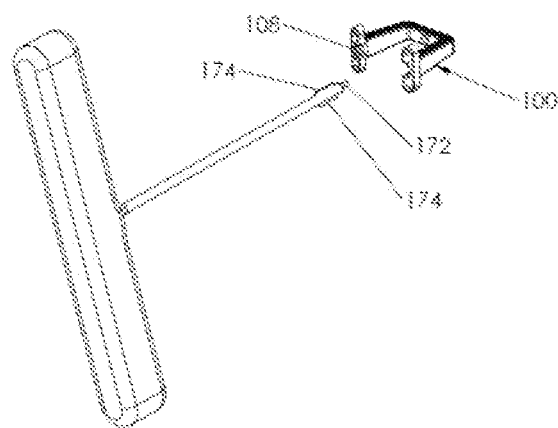
FIGS. 11A and 11B illustrate preferred embodiments of the present invention highlighting the use of a gouge as contemplated herein.
Figure 11B:
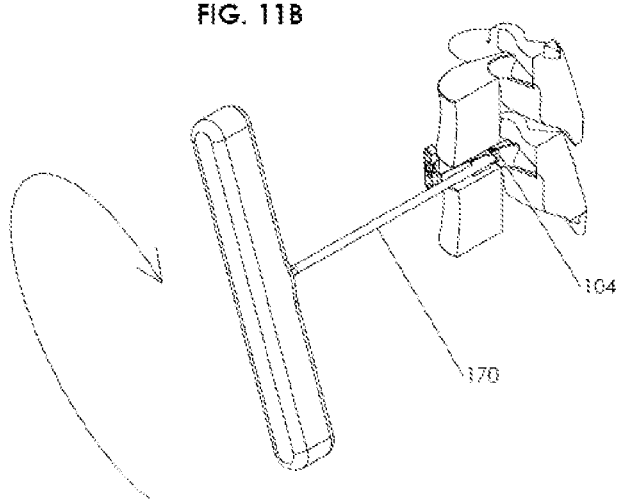
Figure 12A:
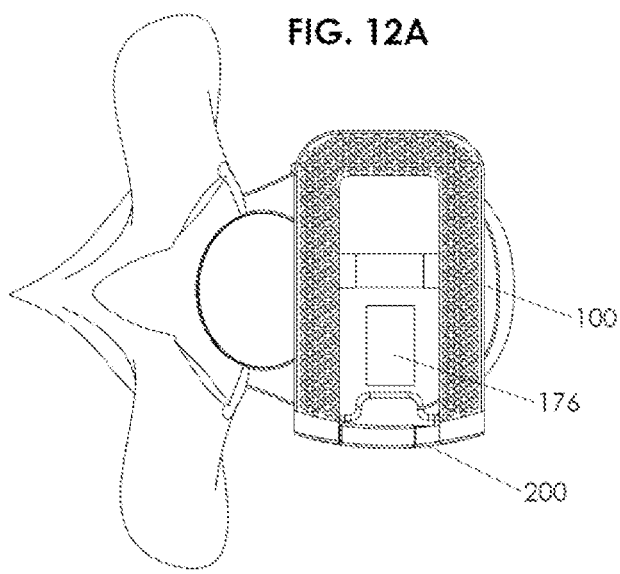

FIGS. 11A, 11B provide further disclosure of a gouge 170 and gouge aligner 104 of the present invention. Generally speaking, a centralizing knob 172 on the gouge is inserted into the gouge aligner 104 and is then rotated by turning the handle. Sharp blades 174 that stick out of the shaft of the gouge 170 and these are driven into the endplates both superiorly and inferiorly to fenestrate the end plates of the vertebrae above and below. FIG. 12A shows a dark region 176 representing the gouged out endplate.

The spacer 100 may also comprise a plurality of spacer protrusions 105 protruding from the anterior portion 102 of the spacer 100 and extending in a superior or an inferior direction. The spacer protrusions 105 may be coupled to the spacer 100, or preferably, they are integral with the spacer 100.

It is important for the surgeon to correctly and accurately position the spacer 100 within the space between the two vertebrae during the surgery. The spacer 100 should not be placed too far in either a posterior or an anterior direction. This can become an issue at times when the bone graft is placed into the spacer 100 because without the spacer protrusions 105 there is a risk that packing the bone graft into the spacer 100 will displace the spacer 100 further in a posterior direction, placing the spinal canal and neural structures at risk of compression, violation, and/or injury. The spacer protrusions 105 ensure that the spacer 100 is not pushed too far in a posterior direction because as the spacer 100 is pushed further and further into the space between the two vertebrae, the spacer protrusions 105 will eventually engage the anterior portion of the two adjacent vertebrae. This engagement will prevent further posterior movement of the spacer 100. In a preferred embodiment, the spacer 100 possesses four spacer protrusions 105, two which are configured to engage the superior vertebra and two which are configured to engage the inferior vertebra. The spacer protrusions 105 can be configured to be fastened to the two adjacent vertebrae. This is preferably accomplished by one or more through-holes 106 on each of the spacer protrusions 105. The spacer protrusions 105 can be fastened to the vertebrae with conventional screws or tacks.

An alternate configuration would be to have spikes built in to the spacer protrusions 105, that would anchor to the vertebrate upon insertion of the spacer 100 into the disc space. The purpose of the spikes or fasteners at the spacer protrusions is to give additional purpose purchase into the vertebral bodies. This allows for a more rigid and solid implant fixation to the spine, reduces motion and therefore increases stability. This added fixation may help support the vertebrae and thereby reduce the incidence of subsidence of the implant into the vertebral and plates.

Figure 10:
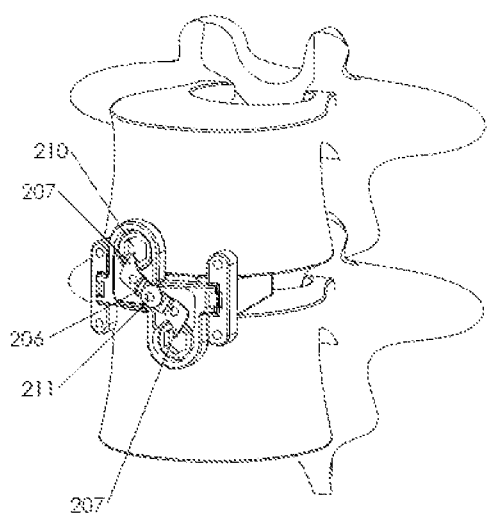
FIG. 10 is a perspective view of a preferred embodiment of the assembled spinal fusion device kit between two adjacent vertebrae with its anti-backout device rotated into position over the fastening devices inserted through the through-holes of the fastener and into the body of the respective vertebra.

In a preferred embodiment, the invention also comprises a fastener, generally indicated at 200, having a posterior side 201 and an anterior side 202, configured to engage the anterior portion 102 of the spacer 100. The fastener can be made of titanium or some other metal. The fastener 200 is configured to be fastened to the two adjacent vertebrae. This is preferably accomplished by a plurality of through-holes 203, 204 on the fastener 200, preferably two or four in number. The fastener 200 can be fastened to the vertebrae with one or more fastening devices 210, such as screws or tacks (but preferably screws) inserted through the through-holes 203, 204 and further inserted into the body of the respective vertebra (e.g. see FIG. 10). In the preferred embodiment, the through-holes 203, 204 are configured to accept and dispose the screws at an angle. Preferably, the superior through-hole 203 is configured to angle the screw into the body of the respective vertebra in a somewhat superior and somewhat medial direction, and the inferior through-hole 204 is configured to angle the screw in a somewhat inferior and somewhat medial direction. It is preferred that the medial directions of the screws be in opposite directions. Thus, for example, if the superior screw is angled toward the patient's left, the inferior screw is preferably angled toward the patient's right. Opposite angling increases the stabilization and pull-out strength of the implant.

As shown in FIG. 3, the fastener 200 may also comprise a fastener locking assembly 208, preferably on opposing sides thereof. The fastener locking assembly 208 operates in conjunction with a correspondingly shaped spacer locking assembly 108, on respective sides of spacer 100, to lock the fastener 200 into place on the anterior portion 102 of the spacer 100. Together, the fastener locking assembly 208 and the spacer locking assembly 108 form a complementary locking arrangement. In a preferred embodiment, the spacer locking assembly 108 and the fastener locking assembly 208 comprise a series of complementary ramps and ridges. This feature allows for successive interlocking between the complementary features on the spacer locking assembly 108 and the fastener locking assembly 208 as the fastener 200 is moved in a posterior direction relative to the spacer 100. In other words, the complementary ramps and ridges will successively "snap" or "lock" into place as the fastener 200 is moved in a posterior direction relative to the spacer 100. Successive interlocking can also be accomplished by other mechanisms. By whatever mechanism is used, the complementary locking arrangement provides a plurality of locking positions of the fastener relative to the spacer.

The fastener 200 may also comprise at least one fastener protrusion 205, protruding from the posterior side 201 of the fastener and extending in a posterior direction. The fastener protrusion 205 also preferably extends in the superior, inferior, and lateral directions such that the fastener protrusion is configured to displace fusion material within the spacer. The fastener protrusion 205 may take on many shapes, including rectangular, ovular, curved, stepped, pointed, edged, trapezoidal, etc. The fastener protrusion 205 is also preferably weight bearing on the adjacent vertebral endplates so that it will resist subsidence into the implant by the vertebrae or subsidence of the implant into the vertebrae. As the fastener 200 engages the anterior portion 102 of the spacer 100, the fastener protrusion 205 will advance into the back-fillable cavity portion of the spacer 100, into which was placed the bone graft/bone substitute material. This action will preferably promote compaction of the bone graft material to maximize the lateral and posterior-anterior filling of the bone graft material within the back-fillable (i.e. cavity) portion of the spacer 100. In this way the fastener assists in compacting and displacing the bone graft material by posterior movement of the fastener toward the spacer.

Additionally, this action will preferably displace some of the bone graft material in a superior and inferior direction against the endplates of the two vertebrae. In other words, the fastener protrusion 205 preferably ensures tight packing of the bone graft material in all dimensions.

Figure 1:
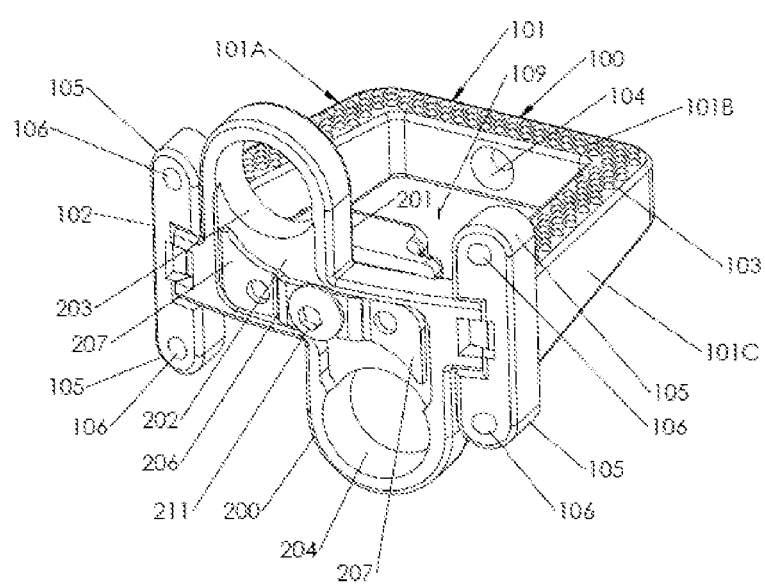
FIG. 1 is a perspective view of a preferred embodiment of the spinal fusion device contemplated within the present invention in an assembled state.
Figure 2:
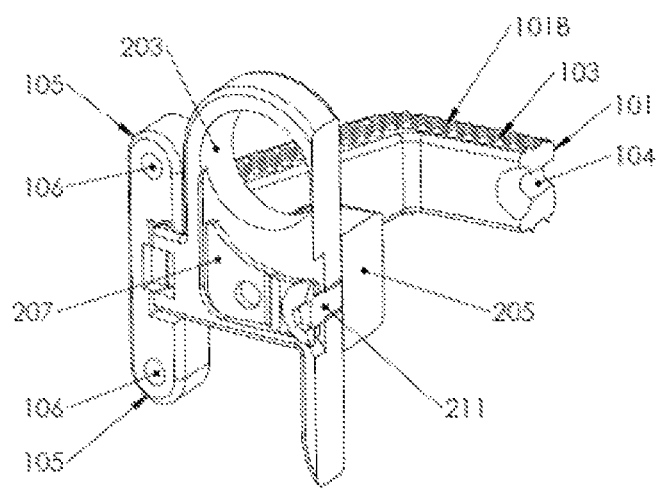
FIG. 2 is a sectional view of a preferred embodiment of the spinal fusion device contemplated within the present invention in an assembled state.

The fastener 200 may also comprise an anti-backout device 206. The anti-backout device 206 operates to prevent the fastening devices (e.g. screws 210) that fasten the fastener 200 to the vertebrae (by being inserted into the body of the respective vertebra) from backing out. Backout can be caused by vibrations, screw breakage, pseudarthrosis, body movement, vertebrae movement, or wear-and-tear on the spinal fusion device in the body, among other things. Backout has the potential to disengage the fastener 200 from the vertebrae or to allow a screw or part of a screw to become free-floating in the soft tissues of the neck. One preferred anti-backout device 206 is illustrated in FIG. 1. A preferred anti-backout device 206 comprises one or more tabs 207 configured to be rotated over the one or more through-holes 203 so as to essentially "trap" the fastening devices 210 therein. This rotation can be accomplished with a locking device 211, such as a hex-nut by way of example and not limitation. In a preferred embodiment, once the fastener 200 is fastened to the vertebrae using screws 210 as discussed above, the locking device 211 can be rotated such that the tabs 207 rotate over the fastening devices 210, thereby blocking the screws from backing out of the vertebrae (see FIG. 10). The anti-backout device 206 can be held in place over the through-holes by simple friction, by biasing threads, by spring-loading the anti-backout device 206 such that it is biased against returning to its original state, or by grooves located on the fastener 200 that allow the tabs 207 to snap or lock into place over the through-holes 203.

The invention contemplated in the foregoing paragraphs has been directed to a spinal fusion device kit. By "kit," it is meant that the spacer 100 and the fastener 200 can be provided assembled together or in an unassembled state; the "kit" can include or not include other items such as the screws discussed above. Embodiments of the present invention are also directed to a method for fusing adjacent vertebrae using the foregoing preferred embodiments of the spinal fusion device kit.

Figure 6:
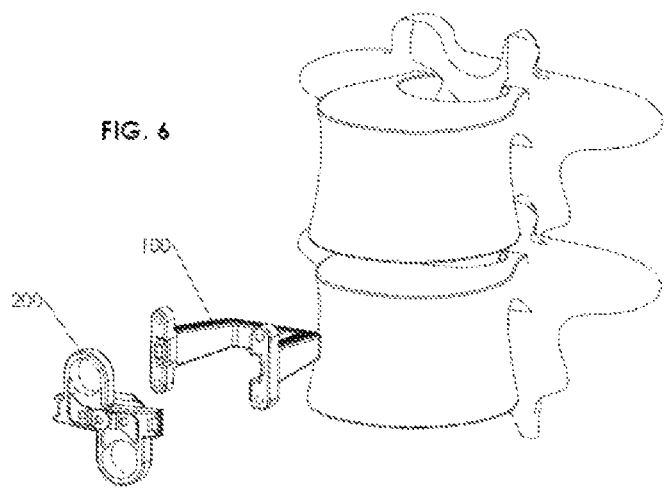
FIG. 6 is a perspective view of a preferred embodiment of the unassembled spinal fusion device kit and two adjacent vertebrae after removal of the disc between them.
Figure 7:
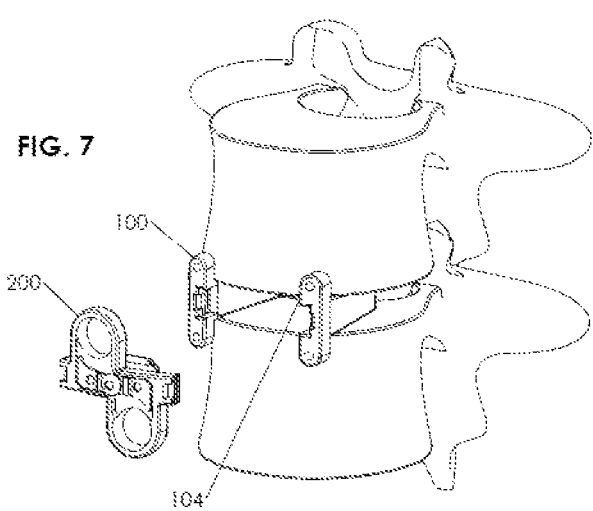
FIG. 7 is a perspective view of a preferred embodiment of the unassembled spinal fusion device kit and two adjacent vertebrae with the spacer of the spinal fusion device kit inserted between the two adjacent vertebrae.
Figure 8:
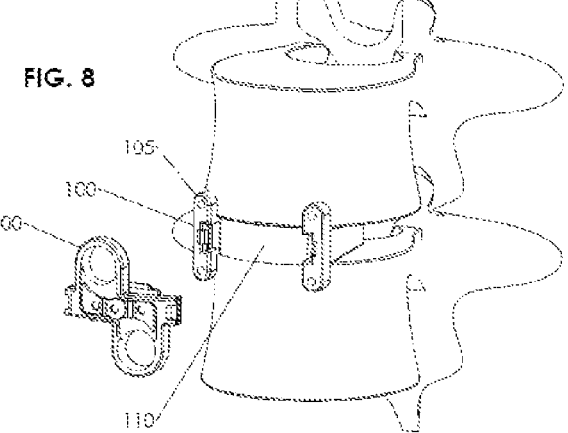
FIG. 8 is a perspective view of a preferred embodiment of the unassembled spinal fusion device kit and two adjacent vertebrae with the spacer of the spinal fusion device kit inserted between the two adjacent vertebrae and packed with bone graft material.

For example, a preferred method for using the spinal fusion device kit is in connection with a surgical procedure as illustrated in FIGS. 6-10. Typically, incisions are made into a patient's skin near the vertebrae sought to be fused. The disc between the two vertebrae is exposed and then removed, as illustrated in FIG. 6, and the back-fillable spacer 100 having a posterior portion and an anterior portion is inserted between the two adjacent vertebrae, as illustrated in FIG. 7. As discussed above, the spacer protrusions 105 limit posterior movement of the spacer 100 once the spacer is fully inserted by engaging the anterior portion of the vertebrae (which includes the cortex of the vertebrae). A gouge is preferably used in conjunction with the gouge aligner 104 to promote controlled superior and inferior endplate fenestration with the purpose of exposing the graft to cancellous bone with its superior blood supply and to bring in increased blood supply to the graft area to increase the odds of obtaining a successful fusion. As illustrated in FIG. 8, bone graft material is inserted into cavity 109 constituting back-fillable portion of the spacer 100.

Figure 9:
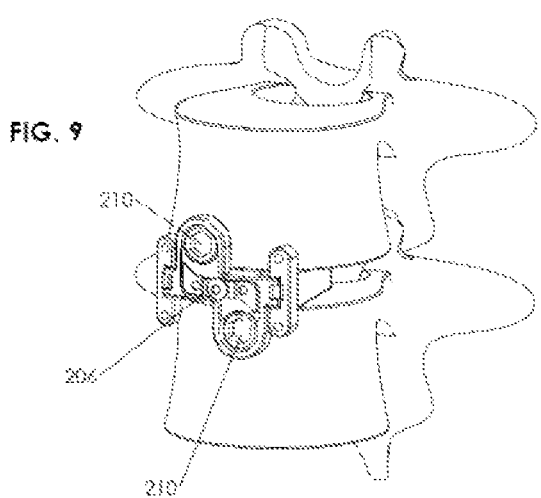
FIG. 9 is a perspective view of a preferred embodiment of the assembled spinal fusion device kit between two adjacent vertebrae.

As illustrated in FIG. 9, the method preferably also comprises the step of engaging the fastener 200 with the anterior portion 102 of the spacer 100. This engagement is preferably accomplished using the complementary locking arrangement 108, 208 on the spacer 100 and the fastener 200, as described above, to provide successive interlocking in a posterior direction. Thus, during the method, the fastener 200 is successively engaged with the spacer 100 as the locking arrangement 108, 208 interacts when the fastener 200 is pushed in a posterior direction into the spacer 100.

The method may also comprise the step of compacting and displacing the bone graft material by utilizing at least one fastener protrusion 205, as described above. Posterior movement of the fastener 200 with a fastener protrusion 205 into engagement with the spacer 100 will compact the bone graft material to maximize its filling of the cavity 109 constituting the back-fillable portion of the spacer 100. Additionally, this motion will preferably also displace some of the bone graft material in a superior and/or inferior direction into greater engagement with the endplates of the two vertebrae.

The preferred method may also comprise the step of fastening the spacer protrusions 105 to the vertebrae. This is preferably accomplished by one or more through-holes 106 on each of the spacer protrusions 105. The spacer protrusions 105 can be fastened to the vertebrae with screws or tacks. The method also comprises the step of fastening the fastener 200 to the two adjacent vertebrae. This is preferably accomplished by a plurality of fastening devices 210 inserted through through-holes 203, 204 on the fastener 200 as disclosed above, being thereafter inserted and fastened to the body of the respective vertebra. As illustrated in the preferred embodiment shown in FIG. 10, one can use anti-backout device 206 to prevent the fastening devices 210 from backing out of the through-holes 203. In a preferred embodiment, the locking device, or in a preferred exemplary embodiment, hex-nut 208, of the anti-backout device 206 is rotated so as to rotate the tabs 207 into position over the screws 210, thereby blocking the screws (or tacks as the case may be) from backing out.

It should also now be understood by one skilled in the art that the surgical procedure according to the present invention may be carried out "laterally" where insertion of the various implant elements is achieved by laterally inserting them into the patient, such as through an incision on the side of the neck or torso. Alternatively, the surgical procedure according to the present invention may be carried out by inserting the various implant elements through an anterior incision, such as on the anterior side of a patient's neck.

Figure 12B:
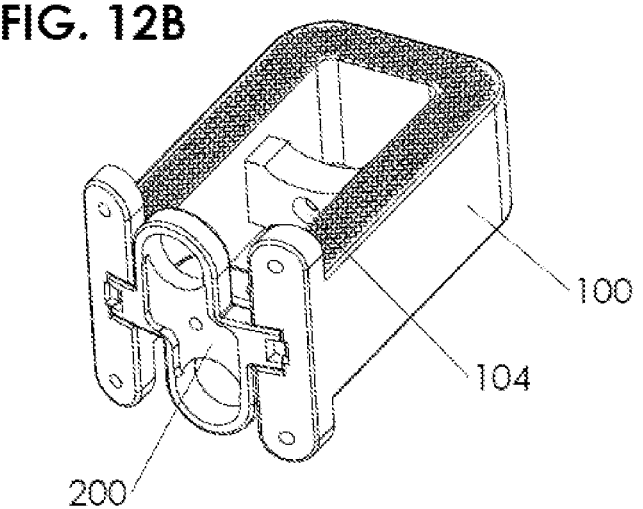

Reference is thus briefly made to FIGS. 12A, 12B, 12C showing an alternative embodiment of the present invention. Differing from the aforementioned device of FIG. 1, for example, it can be seen that the length of the overall spacer 100 in FIGS. 12A, 12B has been elongated, with the gouge aligner 104 preferably being located is on the septum of the elongated back fillable spacer (middle piece). FIG. 12C shows the spacer as implanted in this alternative implanting methodology. In the embodiment of FIGS. 12A-12C, it would be preferable to pre-fill the back end of the spacer and backfill the near end of the spacer. Thus, it would be preferable to insert the gouge into the gouge aligner 104 in the septum, gouging out the near part of the superior and inferior end plates. The septum is provided at least in part to provide strength of the implant.

Based thereon, it should thus be understood that use of "anterior" and "posterior" is for convenience only. That is, while the terms may suggest that one is doing an anterior to posteriorly directed surgery such as anterior cervical discectomy and fusion or anterior lumbar interbody fusion, the disclosure and the claims herein are not so limiting. That is, the present invention, including all embodiments of the device and kit themselves and the disclosed methodology, are equally applicable to the use of and implantation of this device for a lateral interbody fusion. That is, as would be understood by those skilled in the art, when one is doing lateral surgery, all movements/insertions/removals, are made in "lateral to contralateral" directions and not anterior to posterior directions. However, and again for the avoidance of doubt, the use of "anterior" and "posterior" are for reference only and no limitation, other than the position of the claimed features relative to each other (and not the human body in which they may be implanted), is meant thereby nor is to be inferred thereby. In other words, those skilled in the art would appreciate that the terms "posterior" and "anterior" could be equally substituted for the terms "far" and "near," or "opposite" and "first," respectively, as may be preferred, but all of which covers the embodiments disclosed herein. In other words, the present invention, i.e. the device, kit and associated methodologies can be used in a "lateral to lateral" or "lateral to contralateral" orientation. And because of this, the parts of the document that are described as anterior, might also be referred to as "near" or "ipsilateral". Likewise, locations that are described as posterior, could be considered "far" or "contralateral" when applied to lateral surgery.

It will be understood that certain features and subcombinations of the invention are of utility and may be employed without reference to other features and subcombinations. This is contemplated by and is within the scope of the claims. As many possible embodiments may be made of the invention without departing from the scope thereof, it is to be understood that all matter herein set forth or shown in the accompanying drawings is to be interpreted as illustrative and not in a limiting sense. Our invention is solely defined by the following claims.

What is claimed is:

1. A spinal fusion device kit comprising:
   a back-fillable spacer, having a leading portion and a trailing portion, the back-fillable spacer configured to fit between an endplate of a first vertebrae and an endplate of an adjacent vertebrae;
   a fastener, having a leading side and a trailing side, the fastener configured to engage the trailing portion of the spacer and configured to be fastened to the first vertebrae and the adjacent vertebrae; and
   a plurality of spacer protrusions coupled to the trailing portion of the spacer and extending in at least one of a superior and an inferior direction, wherein the plurality of spacer protrusions are configured to engage a cortical bone outside the disc space of the first vertebrae and a cortical bone outside the disc space of the adjacent vertebrae; and
   a gouge aligner formed in the leading portion of the back-fillable spacer for receiving a first end of a gouge; and
   a gouge for fenestrating the endplate of the first vertebrae and/or the endplate of the adjacent vertebrae, wherein the gouge has a first end for insertion into the gouge aligner.

2. The spinal fusion device kit according to claim 1 wherein the plurality of spacer protrusions are integral with the trailing portion of the spacer.

3. The spinal fusion device kit according to claim 1, wherein the leading portion of the back-fillable spacer is in facing alignment with the trailing portion of the back-fillable spacer, and the gouge aligner is a hole or a tab for receiving the first end of the gouge and facilitating alignment of the gouge during a surgery.

4. The spinal fusion device kit according to claim 1 wherein the fastener is lockable into the trailing portion of the spacer by way of a complementary locking arrangement comprising a first part associated with the fastener and a second part associated with the spacer.

5. The spinal fusion device kit according to claim 4 wherein the second part of the complementary locking arrangement on the spacer and the first part of the complementary locking arrangement on the fastener together provide a plurality of locking positions of the fastener relative to the spacer.

6. The spinal fusion device kit according to claim 1 wherein the fastener has at least one fastener protrusion, protruding from the leading side of the fastener, extending in a direction towards the leading portion of the spacer, and configured to displace fusion material within a cavity defined by the spacer.

7. The spinal fusion device kit according to claim 1 wherein the plurality of spacer protrusions are configured to be fastened to the cortical bone outside the disc space of the first vertebrae and the cortical bone outside the disc space of the adjacent vertebrae.

8. The spinal fusion device kit according to claim 1 wherein the spacer has a superior and an inferior side, and wherein at least one of the superior and inferior side is textured.

9. The spinal fusion device kit according to claim 1 wherein the fastener has at least one through hole into which a fastening device is insertable and extendable into the body of one of the two adjacent vertebra, and wherein the spinal fusion device kit comprises an anti-backout device that is positionable in a first position where the anti-backout device does not interfere with the fastening device from being removed from the body of the one vertebra and positionable in a second position where the anti-backout device does interfere with the fastening device from being removed from the body of the one vertebra.

10. The spinal fusion device kit as claimed in claim 1, wherein the gouge comprises at least one blade for fenestrating the endplate of the first vertebrae and/or the endplate of the adjacent vertebrae.

11. The spinal fusion device kit as claimed in claim 10, wherein the gouge comprises two spaced apart blades positioned about a shaft of the gouge, wherein the blades are configured to fenestrate the endplate of the first vertebrae and/or the endplate of the adjacent vertebrae.

12. A spinal fusion device kit comprising:
    a back-fillable spacer, having a leading portion and trailing portion, the back-fellable spacer configured to fit between an endplate of a first vertebrae and an endplate of an adjacent vertebrae and to be secured to a cortical bone outside the disc space of the first vertebrae and a cortical bone outside the disc space of the adjacent vertebrae; and
    a fastener, having a leading side and a trailing side, the fastener configured to engage the trailing portion of the spacer and configured to be fastened to the first vertebrae and the adjacent vertebrae;
    wherein the fastener has at least one fastener protrusion, protruding from the leading side of the fastener, and configured to displace fusion material within a cavity defined by the spacer; and
    a gouge aligner formed in the leading portion of the back-fillable spacer for receiving a first end of a gouge; and
    a gouge for fenestrating the endplate of the first vertebrae and/or the endplate of the adjacent vertebrae, wherein the gouge has a first end for insertion into the gouge aligner.

13. The spinal fusion device kit according to claim 12 wherein the spacer has a plurality of spacer protrusions, protruding from the trailing portion of the spacer and extending in a superior or an inferior direction and wherein the plurality of spacer protrusions are configured to be fastened to the cortical bone outside the disc space of the first vertebrae and the cortical bone outside the disc space of the adjacent vertebrae.

14. The spinal fusion device kit according to claim 12 wherein the fastener is configured to lock into the trailing portion of the spacer by way of a complementary locking arrangement on the fastener and the spacer.

15. The spinal fusion device kit according to claim 12 wherein the fastener has at least one through hole into which a fastening device is insertable and extendable into the body of one of the two adjacent vertebra, and wherein the spinal fusion device kit comprises an anti-backout device that is positionable in a first position where the anti-backout device does not interfere with the fastening device from being removed from the body of the one vertebra and positionable in a second position where the anti-backout device does interfere with the fastening device from being removed from the body of the one vertebra.

16. The spinal fusion device kit as claimed in claim 12, wherein the leading portion of the back-fillable spacer is in facing alignment with the trailing portion of the back-fillable spacer, and the gouge aligner facilitates alignment of the gouge during a surgery.

17. A spinal fusion device kit comprising:
a back-fellable spacer, having a leading edge portion and a trailing edge portion, the back-fellable spacer configured to fit between an endplate of a first vertebrae and an endplate of an adjacent vertebrae;
a fastener, having a leading side and a trailing side, the fastener configured to engage the trailing portion of the spacer and configured to be fastened to the first vertebrae and the adjacent vertebrae; and
a plurality of spacer protrusions coupled to the trailing portion of the spacer and extending in at least one of a superior and an inferior direction, wherein the plurality of spacer protrusions are configured to engage a near cortex of the first vertebrae and a near cortex of the adjacent vertebrae;
a gouge aligner formed in the leading portion of the back-fellable spacer for receiving a first end of a gouge; and
a gouge for fenestrating the endplate of the first vertebrae and/or the endplate of the adjacent vertebrae, wherein the gouge has a first end for insertion into the gouge aligner.

18. A spinal fusion device kit comprising:
a back-fellable spacer, having a leading portion and a trailing portion, the back-fillable spacer configured to fit between an endplate of a first vertebrae and an endplate of an adjacent vertebrae and to be secured to a lateral cortex of the first vertebrae and a lateral cortex of the adjacent vertebrae; and
a fastener, having a leading edge side and a trailing side, the fastener configured to engage the trailing portion of the spacer and configured to be fastened to the first vertebrae and the adjacent vertebrae;
wherein the fastener has at least one fastener protrusion, protruding from the leading edge side of the fastener, and configured to displace fusion material within a cavity defined by the spacer;
a gouge aligner formed in the leading portion of the back-fillable spacer for receiving a first end of a gouge; and
a gouge for fenestrating the endplate of the first vertebrae and/or the endplate of the adjacent vertebrae, wherein the gouge has a first end for insertion into the gouge aligner.

* * * * *